United States Patent
Pudas

(10) Patent No.: US 11,759,100 B2
(45) Date of Patent: Sep. 19, 2023

(54) METHOD AND APPARATUS FOR CLEANING MEDICAL INSTRUMENTS AND FOR DETECTING RESIDUE THEREON

(71) Applicant: PICOSUN OY, Espoo (FI)

(72) Inventor: Marko Pudas, Espoo (FI)

(73) Assignee: PICOSUN OY, Espoo (FI)

( * ) Notice: Subject to any disclaimer, the term of this patent is extended or adjusted under 35 U.S.C. 154(b) by 421 days.

(21) Appl. No.: 16/830,329

(22) Filed: Mar. 26, 2020

(65) Prior Publication Data

US 2020/0305701 A1 Oct. 1, 2020

Related U.S. Application Data

(60) Provisional application No. 62/826,408, filed on Mar. 29, 2019.

(51) Int. Cl.
| | | |
|---|---|---|
| *A61B 1/12* | (2006.01) | |
| *A61B 1/00* | (2006.01) | |
| *A61L 2/20* | (2006.01) | |
| *C23C 16/455* | (2006.01) | |

(52) U.S. Cl.
CPC .......... *A61B 1/126* (2013.01); *A61B 1/00103* (2013.01); *A61L 2/20* (2013.01); *C23C 16/45544* (2013.01); *A61L 2202/24* (2013.01)

(58) Field of Classification Search
CPC . A61B 1/121; A61B 90/70; A61B 2090/0813; A61B 2090/0814; A61B 2090/701; A61B 2090/702; A61L 2/28; A61L 2202/24; G01N 31/226
See application file for complete search history.

(56) References Cited

U.S. PATENT DOCUMENTS

| | | | | |
|---|---|---|---|---|
| 5,482,684 A | * | 1/1996 | Martens | A61L 2/28 435/31 |
| 5,518,927 A | * | 5/1996 | Malchesky | A61L 2/28 436/1 |
| 6,027,572 A | | 2/2000 | Labib et al. | |
| 2003/0012689 A1 | * | 1/2003 | Caputo | A61L 2/208 422/123 |
| 2009/0068057 A1 | * | 3/2009 | Spenciner | A61L 2/28 422/3 |
| 2014/0127270 A1 | | 5/2014 | Amarnamni | |

(Continued)

FOREIGN PATENT DOCUMENTS

| | | |
|---|---|---|
| CN | 1422165 A | 6/2003 |
| CN | 107551296 A | 1/2018 |

(Continued)

OTHER PUBLICATIONS

Extended European Search Report issued in European Patent Application 20 165 565.1 dated Aug. 18, 2020.

(Continued)

*Primary Examiner* — Aaron B Fairchild
*Assistant Examiner* — Stephen Floyd London
(74) *Attorney, Agent, or Firm* — NIXON & VANDERHYE

(57) ABSTRACT

A method for cleaning a medical instrument and for detecting residue thereon is provided in which method a non-sterile or conventionally sterilized medical instrument is exposed to pressure below 100 hPa, and, subsequently, exposed to at least one gas reactive to the residue.

11 Claims, 1 Drawing Sheet

(56) References Cited

U.S. PATENT DOCUMENTS

| | | | |
|---|---|---|---|
| 2015/0374868 A1* | 12/2015 | Bruce | A61L 2/26 422/119 |
| 2017/0252471 A1 | 9/2017 | Patel | |
| 2017/0252472 A1* | 9/2017 | Dang | A61B 1/00062 |
| 2018/0000976 A1* | 1/2018 | Nowruzi | A61L 2/208 |
| 2018/0125606 A1* | 5/2018 | Labib | A61B 1/12 |
| 2018/0207307 A1* | 7/2018 | Schwartz | A61L 2/10 |
| 2020/0171244 A1* | 6/2020 | Weikart | A61L 2/0094 |

FOREIGN PATENT DOCUMENTS

| | | |
|---|---|---|
| DE | 102016004043 A1 | 10/2017 |
| EP | 0 201 553 A1 | 11/1986 |
| EP | 1 166 802 A2 | 1/2002 |
| EP | 1 166 802 A3 | 5/2003 |
| EP | 3 263 138 A1 | 1/2018 |
| JP | S54-152389 A | 11/1979 |
| WO | WO-02070025 A1 * 9/2002 ............... A61L 2/14 |
| WO | 2018/218013 A2 | 11/2018 |

OTHER PUBLICATIONS

Office Action issued in Chinese Patent Application No. 202010228943.5 dated Jan. 31, 2023.

* cited by examiner

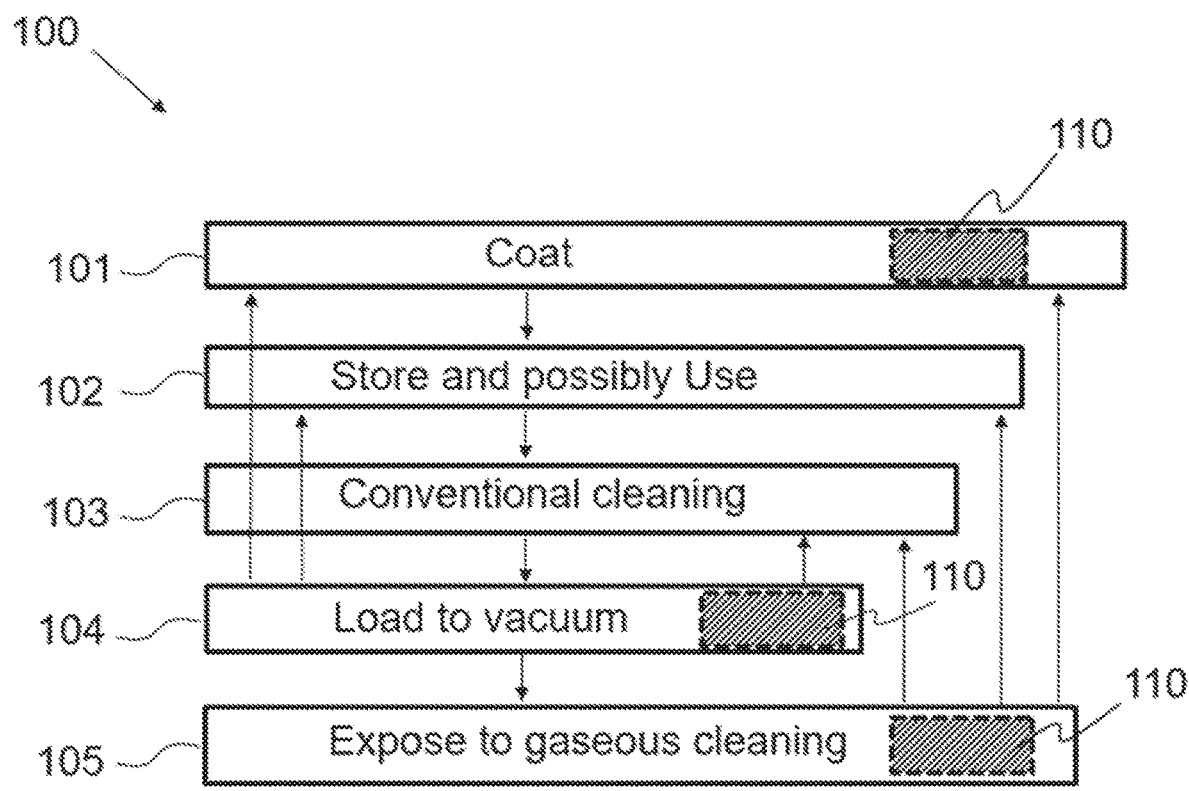

METHOD AND APPARATUS FOR CLEANING MEDICAL INSTRUMENTS AND FOR DETECTING RESIDUE THEREON

FIELD OF THE INVENTION

The present invention generally relates to equipment and methods for cleaning medical instruments. In particular, the invention relates to equipment and methods that allow, in addition to cleaning, for detecting presence of contamination traces and analyzing the same on said medical instruments.

BACKGROUND OF THE INVENTION

Medical and surgical procedures often require use of multipart instruments often comprising prominent features and/or narrow cavities or channels. Additionally, said medical instruments may be made of different materials, including metal, glass, ceramics and/or plastics. Exemplary multipart gear include general surgical, microsurgical and dental instruments, as well as endoscopes.

An endoscopy is a medical procedure that involves exploration of the interior of a hollow body cavity or an organ. Endoscopes, either flexible (for example, gastroscope, duodenoscope, colonoscope, sigmoidoscope, enteroscope, nasopharyngoscope, bronchoscope) or rigid (some bronchoscopes, laparoscopes) are used in diagnostics and treatment of human diseases and are readily contaminated by body fluids and secretions.

Flexible endoscopes are complex devices containing fiber optics and narrow channels inside a tubular sheath. While the outer surface of a tubular endoscope does not pose a problem for cleaning, disinfecting and ultimately for sterilization; small instruments to be inserted inside the body, as well as other channel- and tube-shaped devices used to introduce tools for tissue sampling or for surgical operations, to coagulate bleeding or for other purposes, such as suctioning and injecting fluids, are challenging to sterilize. In particular, flexible endoscopes are made of materials, which do not tolerate high temperature sterilization and there is a risk of inadequate sterilization due to the length of the instrument with regard to its' narrow (small diameter) channel(s).

At present, the endoscopes, as well as the other medical instruments, which need to be inserted inside the human body, are often cleaned using manual labor and liquid substances aiming at disinfecting the instrument by utilizing a flow of said substance through the endoscope. The situation aggravates with the fact that due to the long channels inside the endoscopes, it is challenging to monitor the result of sterilization process; therefore, a majority of cleaned endoscopes still contains microorganisms posing threat for the patients, in terms of transfer of hazardous microorganisms from a patient to another. The resistance of bacteria to sterilization can be explained by formation of biofilm inside the endoscope channels, which resists sterilization efforts.

Certain sterilization methods utilize gases, optionally in vacuum, to sterilize medical. Gaseous sterilants include ethylene oxide, formaldehyde and hydrogen peroxide, as discussed, for example, in US2017/0252471 A1 (Patel). However, all mentioned compounds are toxic, likely to leave residue and/or require extensive washing thereafter.

In fact, all above mentioned medical or surgical instruments, including, but not limited to endoscopes, represent a substantial piece of investment made by a health care facility; therefore, proper handling and cleaning of these instruments is important to reduce expenditure.

In this regard, an update in the field of monitoring the cleaning efficiency of a cleaning activity associated with sterilizing medical device for multiple use is still desired. In particular, the challenges associated with cleaning of complex, multipart medical devices, such as endoscopes, should be addressed.

SUMMARY OF THE INVENTION

An objective of the present invention is to solve or to at least alleviate each of the problems arising from the limitations and disadvantages of the related art. The objective is achieved by various embodiments of a method and a related apparatus for cleaning a medical instrument and for detecting residue, such as organic residue, thereon.

In an aspect, a method for cleaning a medical instrument and for detecting residue thereon is provided according to what is defined in independent claim 1.

In embodiment, the method comprises: (a) obtaining a non-sterile or conventionally sterilized medical instrument; (b) loading said instrument into a deposition and/or analysis apparatus; (c) exposing said instrument to pressure below 100 hPa; and (d) exposing said instrument to at least one gas reactive to the residue.

In embodiment, the method further comprises pre-applying at least part of the medical instrument obtained at (a), with a chemically deposited coating. In embodiment, the coating is pre-applied onto at least a part of said instrument by Atomic Layer Deposition (ALD).

In embodiment, the instrument is exposed, at (c) to a pressure below 10 hPa, preferably below 1 hPa, most preferably below 0.1 hPa.

In embodiment, the instrument is exposed, at (d), to at least one gas reactive to the residue, wherein said at least one gas contains at least one chemical substance reactive to the residue.

In embodiment, the medical instrument is a multi-part medical instrument, such as an endoscope.

In embodiment, the method comprises detecting and/or quantifying the residue, at least during (c) and/or (d), by at least one sensor device. In embodiment, said at least one sensor device is configured to detect and/or quantify the residue in at least a part of a gas flow being evacuated from the deposition and/or analysis apparatus.

In embodiment, the method comprises reverting the medical instrument to the procedure of cleaning and/or sterilization by conventional methods if concentration of the residue detected and/or quantified at any one of (c) and (d) exceeds a predetermined threshold.

In embodiment, the method comprises subjecting the medical instrument to disposal if concentration of the residue detected and/or quantified at (d) pertains to a predetermined level.

In an aspect, a deposition and/or analysis apparatus for cleaning a medical instrument and for detecting residue thereon is provided, according to what is defined in the independent claim 11.

In embodiment, the apparatus comprises at least one reaction chamber configured to receive a medical instrument or medical instruments, in which reaction chamber said medical instrument is exposed to pressure below 100 hPa and, subsequently, to an at least one gas reactive to the residue to be detected.

In embodiment, the apparatus is configured as a chemical deposition reactor. In embodiment, the apparatus is configured as an Atomic Layer Deposition reactor. In embodiment, the apparatus comprises at least one sensor device to detect and/or analyze the residue.

In another aspect, use of a deposition and/or analysis apparatus of some previous aspect is provided for cleaning a medical instrument or instruments and for detecting residue thereon, according to what is defined in the independent claim 15. In embodiment, the medical instrument is a multi-part medical instrument, such as an endoscope.

Without limiting the scope and interpretation of the patent claims, certain technical effects of one or more of the example embodiments disclosed herein are listed in the following.

The method and apparatus disclosed hereby allow for efficient cleaning of medical instruments otherwise challenging to clean (e.g. multipart medical instruments and/or long tubular medical instruments with internal cavities/channels, such as endoscopes). Chemical substances supplied in a gas phase fill smaller cavities better than any liquids (e.g. compared to conventional washing). The method disclosed hereby thus allows for destroying all kinds of microorganisms present on the surfaces of said medical instrument, e.g. bacteria, whether present in single colonies or as a resistant biofilm, as well as viruses and prions.

The invention offers a significant benefit, that, in addition to undergoing the efficient cleaning process, the medical instruments are also analysed for the presence of any traces of organic contamination, decomposition products and/or other residue. The method can be used to verify that the item is clean. In other words, the invention allows cleaning medical instruments once used to a level that is normally attainable only at a manufacturing facility when (new) instruments are packed into sterilized packages. Such purity level cannot be attained/controlled by conventional cleaning and/or sterilizing (e.g. autoclave sterilizing) methods.

Utilisation of chemical deposition technologies, such as ALD, enables coating of cavities and (nano)pores with extremely high aspect ratios of more than 1000:1. Furthermore, improved performance for pipe-like instruments, for example, can be obtained by propagating the gases through said pipes with a suitable flow arrangement. Another benefit of the ALD deposited firm is that it creates smooth conformal surface(s), which enhance(s) the flow of fluids therealong. In some instances, a fluid-repelling coating material can be applied. In similar manner, the ALD-deposited film can be configured to reduce fluid adhesion that will facilitate traditional cleaning in any further use of the instrument.

It may occur that in some conventional treatments, e.g. upon ozone treatment, certain parts of a medical instrument, e.g. plastic parts, are erroneously recognized as an undesired residue. A conformal coating comprising at least one metal compound and (pre)applied to the medical instrument shall prevent those (plastic) parts from being exposed to harsh conditions of conventional cleaning and/or analysis or at least decrease such exposure.

The invention further provides versatility in view of categorising the medical instruments to those that require/not require additional cleaning and to those that must be subjected to disposal (cannot be efficiently cleaned anymore).

Being capable of performing classification as above, with high reliability, the invention allows for more efficient reuse of medical instruments; therefore, costs associated with purchasing of new medical instruments can be decreased.

In the present disclosure, materials with a layer thickness below 1 micrometer (μm) are referred to as "thin films".

The expression "a number of" refers herein to any positive integer starting from one (1), e.g. to one, two, or three; whereas the expression "a plurality of" refers herein to any positive integer starting from two (2), e.g. to two, three, or four.

The terms "first" and "second" are not intended to denote any order, quantity, or importance, but rather are used to merely distinguish one element from another.

BRIEF DESCRIPTION OF THE DRAWINGS

The invention will now be described, by way of example only, with reference to the accompanying drawings, in which:

FIG. 1 is a flow chart of a method according to an embodiment.

DETAILED DESCRIPTION

The invention, according to one aspect, pertains to provision of a method for cleaning a medical instrument and for detecting residue thereon (FIG. 1). By the term "residue", we refer to any essentially solid remainings or debris, primarily of organic nature, accumulated or lodged on/in the medical/surgical instrument during its normal use, e.g. cell mass, cellular network debris, ambient contamination and the like. Due to the nature of the instrument to be cleaned, the residue to be detected mostly organic; however, the method can be adjusted such, as to detect essentially inorganic matter and/or a combination of organic and inorganic residue.

The method starts with obtaining an item, such as a medical instrument. In present disclosure, the medical instrument thus obtained is a non-sterile medical instrument stored (in a storage room, for example) and optionally used (102) or a medical instrument sterilized by conventional methods (103). By conventional use we refer to use of the medical instrument during patient examination and/or therapeutic- or surgery treatment, optionally cleaned and/or sterilized by conventional methods (washing, autoclaving, etc.).

The medical instrument can be any reusable (multi-use) instrument used in medical examination, dental- and/or surgical operations/interventions executed on human patients or on non-human animals.

In some instances, said medical device is provided as an elongated body with an internal channel, a cavity and/or any one of the internal and external features, such as protruding parts or recesses, e.g. grooves.

The medical instrument can be configured as a flexible or rigid endoscope device or an assembly including any auxiliary appliances provided with said endoscope assembly and being in need for cleaning. Endoscopic devices and related assemblies include, but are not limited to: gastroscopes, duodenoscopes, colonoscopes, sigmoidoscopes, enteroscopes, laparoscopes, thoracoscopes, nasopharyngoscopes, bronchoscopes, laryngoscopes, colposcopes, cystoscopes, ureteroscopes, and arthroscopes.

In some configurations, an insert or a similar arrangement can be placed at least at one end of the endoscope. In such an event, differential pressure of air or other gas, such as inert gas, for example, can be generated across the channels of the endoscope.

At 102, the item is thus stored and/or used as indicated above (e.g. in common medical practice). At 103, the item is cleaned/sterilized by conventional methods.

Step 103 may be omitted, if the item has been obtained from a sealed/sterilized package, for example, but not used, in a meaning, not used in medical practice.

At least a part of the medical instrument can be pre-applied, at 101, with a coating deposited by a method of chemical deposition in gaseous (vapour) phase, such as Atomic Layer Deposition (ALD) or, alternatively, Chemical Vapour Deposition (CVD). In some instances, the coating comprises at least one metal compound.

The basics of an ALD growth mechanism are known to a skilled person. ALD is a special chemical deposition method based on the sequential introduction of at least two reactive precursor species to at least one substrate. It is to be understood, however, that one of these reactive precursors can be substituted by energy when using, for example, photon-enhanced ALD or plasma-assisted ALD, for example PEALD, leading to single precursor ALD processes. For example, deposition of a pure element, such as metal, requires only one precursor. Binary compounds, such as oxides can be created with one precursor chemical when the precursor chemical contains both of the elements of the binary material to be deposited. Thin films grown by ALD are dense, pinhole free and have uniform thickness. In some instances, Chemical Vapour Deposition (CVD) may be utilized.

The at least one substrate is typically exposed to temporally separated precursor pulses in a reaction vessel to deposit material on the substrate surfaces by sequential self-saturating surface reactions. In the context of this application, the term ALD comprises all applicable ALD based techniques and any equivalent or closely related technologies, such as, for example the following ALD sub-types: MLD (Molecular Layer Deposition), plasma-assisted ALD, for example PEALD (Plasma Enhanced Atomic Layer Deposition) and photon-enhanced Atomic Layer Deposition (known also as photo-ALD or flash enhanced ALD). The process can also be an etching process, one example of which being an ALE process. It should be noted that with PEALD and photon-enhanced ALD, the additive treatment can be limited to the surfaces visible to the radiation source.

ALD is based on alternating self-saturative surface reactions, wherein different reactants (precursors) provided as chemical compounds or elements in a nonreactive (inert) gaseous carrier are sequentially pulsed into a reaction space accommodating a substrate. Deposition of a reactant is followed by purging the substrate by inert gas. Conventional ALD deposition cycle proceeds in two half-reactions (pulse A-purge A; pulse B-purge B), whereby a layer of material is formed in a self-limiting (self-saturating) manner, typically being 0.05-0.2 nm thick. Typical substrate exposure time for each precursor ranges within 0.01-1 seconds.

Pulse A comprises a first precursor in a gaseous phase (first precursor vapor) and pulse B comprises a second precursor in a gaseous phase (second precursor vapor). Inactive gas and a vacuum pump are typically used for purging gaseous reaction by-products and the residual reactant molecules from the reaction space during purge A and purge B. A deposition sequence comprises at least one deposition cycle. Deposition cycles are repeated until the deposition sequence has produced a thin film or coating of desired thickness. Deposition cycles can also be either simpler or more complex. For example, the cycles can include three or more reactant vapor pulses separated by purging steps, or certain purge steps can be omitted. On the other hand, photo-enhanced ALD has a variety of options, such as only one active precursor, with various options for purging. All these deposition cycles form a timed deposition sequence that is controlled by a logic unit or a microprocessor.

It is thus preferred that the coating is applied to at least a part of the medical instrument by ALD.

ALD process used alone or in combination with the other chemical deposition processes can be used to render the coated surfaces (super)hydrophobic or (super)omniphobic. The latter refers to ability of the surface to repel almost any fluid. Superhydrophobic surfaces are generally defined as the surfaces having a contact angle of a water droplet greater than 150 degrees.

Although ALD thin-film coating may not be mechanically very durable, the ALD process enables regeneration of intrinsic hydrophilic or hydrophobic properties of the substrate surface. In other words, the ALD process restores the properties intrinsic to some particular substrate surface before said surface has been used and became contaminated during such use. Further, if the substrate originally contains a number of features, e.g. nanostructures or similar, by virtue of which features the substrate is rendered with certain properties (hydrophobic, hydrophilic, etc.), these features become easily blocked or covered up with the residue, such as cell mass debris for example, during use. The method disclosed hereby provides for efficient cleaning of the substrate and its features to restore these properties.

Referring back to FIG. 1, the at least one coating layer pre-applied, at 101, onto at least part of the medical instrument, can be configured such, as to prevent residing of matter resulting from a majority of cleaning processes applied to the instrument itself (e.g. washing agents, ozone cleaning, etc.). Additionally or alternatively, the coating layer can hinder or prevent the residue from adhering onto said item during its use (e.g. in medical/surgical applications).

The coating can be made with a biocompatible metal oxide, for example. By way of example, biocompatible metal oxides include, but are not limited with: magnesium oxide (MgO), zinc oxide (ZnO), titanium (di)oxide ($TiO_2$), and zirconium (di)oxide ($ZrO_2$). Any other suitable compound can be utilized.

Sufficiently thin layer of metal oxide, such as about 1-10 nm layer, does not hinder flexibility of the surfaces and can be used on bending plastic parts, for example. Depending on the coating material and the bend radius, the coating layer having thickness within a range of about 0.1 nm to about nm 50 nm is considered sufficiently flexible.

The topmost layer(s) of the coating 101 (last deposited) can be made of organic material, which can facilitate cleaning procedures and can be eventually reacted with ozone ($O_3$), for example. Mentioned reaction(s) of organic material with ozone or another compound with similar mode of action leads to destruction of organic matter followed by its removal/withdrawal out of a reaction space.

The method continues with loading optionally pre-coated medical instrument(s) into a deposition and/or analysis apparatus with a reaction chamber, in where the instrument(s) is/are exposed to a predetermined reaction environment. In said apparatus/reaction chamber, the instrument(s) is/are exposed to a predetermined pressure (104) and to at least one gaseous compound (precursor) reactive to the residue to be detected (105). Steps 104 and 105 can be performed sequentially or simultaneously.

The apparatus is preferably configured to exploit principles of vapor-deposition based techniques. In terms of an overall implementation, the reactor 100 may be based on an ALD installation trademarked as Picosun R-200 Advanced ALD system available from Picosun Oy, Finland. Nevertheless, the features underlying a concept of the present invention can be incorporated into any other chemical deposition reactor embodied as an ALD, MLD (Molecular Layer Deposition) or CVD device, for example.

Mentioned apparatus comprises a reaction chamber, with a reaction space (deposition space) established by an interior thereof. The reactor further comprises a number of appliances configured to mediate fluidic flow (inert fluids and reactive fluids containing precursor compounds P1, P2) into the reaction chamber. Mentioned appliances are provided as a number of intake lines/feedlines and associated switching and/or regulating devices, such as valves, for example.

Precursor(s) P1, P2 are delivered into the reaction space in an essentially gaseous form. Reactive fluid entering the reaction chamber through at least one feedline is preferably a gaseous substance comprising a predetermined precursor chemical carried by an inert carrier (gas). Delivery of the precursor chemicals into the reaction space and film growth on the substrate is/are regulated by means of the abovesaid regulating appliances, such as e.g. three-way ALD valves, mass-flow controllers or any other device suitable for this purpose.

The apparatus further comprises an evacuation line for discharging an exhaust flow out of the reaction chamber. The evacuation line constitutes a fore-line for an evacuation pump and it may comprise, in some configurations, a closing valve, preferably upstream the pump unit. Such pump foreline assembly can further comprise means that enable the reactions with chemicals utilized, and/or means for neutralizing and/or removing said chemicals from the apparatus. Mentioned means include, but are not limited to generally known ALD tools and appliances, such as any one of: an afterburner device (provides for mixing of reactive gases), a trap (provides for adsorption of chemicals and prevents the outflowing particles of matter from flowing into the pump), a scrubber, or a combination of the abovesaid. It is preferred that withdrawal of fluidic substance from the reaction chamber is implemented in an uninterrupted manner, whereby the pump, preferably configured as a vacuum pump, removes fluidic substance from the reaction chamber continuously during the entire deposition process.

The instrument(s) loaded into the reaction chamber of the apparatus is/are exposed, at 104, to pressure essentially equal to or below of about 100 hectopascal (hPa). In some instances, the instrument(s) is/are exposed to pressure essentially equal to or below of about 10 hPa, preferably, essentially equal to or below of about 1 hPa, most preferably, essentially equal to or below of about 0.1 hPa. It is preferred that vacuum conditions are created in the apparatus/reaction chamber.

In some instances, the step 104 can include adjusting temperature in the reaction chamber to a predetermined level, at which liquid, present in the residue, such as contamination-, decomposition- or degradation traces of primarily organic nature, residing on the medical instrument, starts to vaporize/evaporate. In some instances, the reaction chamber can be heated to e.g. 100 degrees Celsius (° C.) or higher. Indicated temperature can be below 100° C., such as, within a range of about 20° C. to about 100° C., in presence of reactive chemicals required to produce the desired (cleaning) effect.

By subjecting the medical instrument(s) to vacuum conditions optionally combined with elevated temperature, at step 104, the instrument(s) is/are cleaned off the impurities/residue.

At 105, the instrument(s) is/are exposed to at least one gas comprising or consisting a precursor compound reactive to the residue. Thus, the entire instrument item(s) is/are exposed to a flow of reactive gas containing at least one chemical substance, with essentially cleaning properties, including, but not limited to oxygen ($O_2$), ozone ($O_3$), trimethylaluminium (TMA), titanium tetrachloride ($TiCl_4$), formic acid ($CH_2O_2$) and ammonia ($NH_3$).

It should be noted that ALD uses many chemicals that are not stable in the ambient (e.g. atmospheric air). When exposed to e.g. air, said chemicals, such as TMA, decompose to form harmless compounds.

Many common ALD reaction(s) utilize titanium tetrachloride ($TiCl_4$), such as for depositing titanium oxide ($TiO_2$) from $TiCl_4$ and water. In this regard, it should be noted that although $TiCl_4$ is generally toxic gas (suitable for sterilization), only negligible amounts thereof are used in ALD and, additionally, any residual $TiCl_4$ can be further neutralized with an appropriate compound provided in gaseous phase, such as ammonium gas ($NH_3$), for example.

If used, as a common compound, at any one of stages 101, 104 and 105, $TiCl_4$ may enter side reactions with the surface hydroxyl (OH—) groups, which will result in formation of hydrochloric acid (l-ICl). As described above for $TiCl_4$, also hydrochloric acid can be neutralized with $NH_3$, for example, to yield harmless salts, such as ammonium chloride ($NH_4Cl$) in present example.

In PEALD reactor conditions, highly reactive ions and free radicals of the gaseous elements, such as hydrogen, are typically formed. These highly reactive species react with the surfaces and effectively clean them out.

In some instances, the medical instrument is exposed to such precursors that cause degradation of organic matter residing on- or adhered to the exposed surfaces of the medical instrument, e.g. ozone ($O_3$). Exposure of the contaminated medical instrument to ozone pulse(s) results in formation of $CO_2$ that can be detected by related sensor devices (see below). When (precursor) compounds capable of destroying/decomposing organic matter react with the residue on the medical instrument, degassing of said organic matter occurs accompanied with $CO_2$ release, detectable as mentioned above.

Gas flow may be allowed to penetrate through irregularities present on/within the medical instrument, such as pores, holes, channels, cavities, and the like. Alternatively, gas flow may be passed or forced through these irregularities in a separate action (e.g. by establishing a targeted gaseous flow stream).

It is preferred that said at least one gas contains a chemical substance reactive to the residue.

In embodiment, at least during stages 104 and 105 the residue is detected and/or quantified by at least one detector/sensor device 110. The sensor device 110 can be configured as a Residual Gas Analyzer (RGA) device, such as a mass spectrometer. The device 110 is configured to measure and/or to quantify the matter exhausted from the reaction space (in where the medical instrument(s) is/are placed) with the outgoing gas flow.

Each of the sensor devices 110 is configured to detect and/or quantify the residue in at least a part of a gas flow being evacuated from the deposition and/or analysis apparatus (namely, from the reaction chamber).

The sensor can be configured to simply measure an amount of vaporized matter (vapour originating from degassing of the residual matter). Additionally or alternatively, the sensor can be configured to detect and quantify the amount of precursor chemicals and/or the products of chemical reactions, in the exhaust gaseous flow. Depending on results, the process can continue according to a number of exemplary strategies. The following approaches can be adopted:

(i) if the item (the medical instrument) is assumed to be clean (not used in medical practice/operations) and no organic matter, such as carbon dioxide ($CO_2$), has been detected by means of the appropriate sensor 110 during and/or after degassing the item with a chemical compound causing decomposition of organic matter, such as ozone ($O_3$), for example (at stage 105), further processing of said item, such as (pre)coating 101 can be omitted. The item is then ready for use.

(ii) If significant organic contamination (above a predetermined threshold) has been detected and/or measured during and/or after degassing as described at (i), the treatment 105 time period can be extended, or (iii) If significant organic contamination (above a predetermined threshold) has been detected and/or measured during and/or after the degassing as described at (i), the item may be returned to washing 103 to remove as much contamination as possible. Thus, in condition that the concentration of the residue detected and/or quantified at step 104 and/or 105 exceeds a predetermined threshold, the medical instrument is reverted to the procedure of cleaning and/or sterilization by conventional methods. The threshold value is set individually for each batch and/or a series of batches (i.e. the reactor loads) depending on the instrument to be cleaned, expected contaminants to be analyzed, utilized gaseous phase and precursor compounds, and the like.

Different thresholds can be set to differentiate scenarios (ii) and (iii) from one another. Alternatively, essentially same threshold values (ii, iii) may be adopted. (iv) if during the ALD (pre)coating 101 and/or during any one of the stages 104, 105 conducted in the reaction chamber, measured residual gas concentrations do not drop to acceptable levels, it can be determined that the item is no longer viable for use and must be subjected to disposal. Thus, if an item has been reverted (e.g. once) to conventional washing, and even after that, in condition that the concentration of the residue detected and/or quantified at any one of stages 101, 104 and 105 still pertains to a predetermined level (exceeds the threshold(s) as pointed out at (ii) and (iii)), said item/medical instrument is subjected to disposal.

From any one of the stages 104 and 105 the item can be returned to washing 103, storing and usage 102 and for coating or re-coating 101 (see arrows pointing upwards, FIG. 1), until it could be determined, at 105, that said item must be disposed. The item can be reverted to 101, if the coating needs to be re-applied onto said item.

It is preferred that detection and/or quantification of the residue is conducted also during initial coating of the item (stage 101).

In some instances, a conventional cleaning procedure 103 can be omitted.

In an aspect, a deposition and/or analysis apparatus for cleaning a medical instrument and for detecting residue thereon is provided, according to what has been described hereinabove. The apparatus comprises at least one reaction chamber configured to receive a medical instrument or medical instruments, in which reaction chamber said medical instrument is exposed to pressure below 100 hPa and, subsequently, to an at least one gas reactive to the residue.

The deposition and/or analysis apparatus is preferably configured as a chemical deposition reactor, such as an Atomic Layer Deposition reactor. The apparatus is preferably equipped with at least one sensor device 110 disposed in the reaction chamber and/or downstream said reaction chamber, e.g. in the vacuum pump fore-line, in connection with the reaction chamber or disposed after the pump.

In further aspect, use of a deposition and/or analysis apparatus according to some previous aspect is provided for cleaning a medical instrument and for detecting residue thereon. In embodiment, said use is provided for cleaning- and for detecting residue on the multipart medical instrument, such as an endoscope.

The above description of the method and the apparatus according to the present invention is equally compatible and fully applicable for sterilization and/or for verification of a required level of sterilization of the items used in space crafts and in extraterrestrial rovers and of the related sample containers.

It shall be appreciated by those skilled in the art that the embodiments set forth in the present disclosure may be adapted and combined as desired. The disclosure is thus intended to encompass any possible modifications of the device and the deposition method, recognizable by those of ordinary skill in the art, within a scope of appended claims.

The invention claimed is:

1. A method for cleaning a medical instrument and for detecting residue thereon, comprising:
    (a) obtaining a non-sterile or conventionally sterilized medical instrument;
    (b) loading said medical instrument into a deposition and/or analysis apparatus;
    (c) exposing said medical instrument to pressure below 100 hPa,
    (d) exposing said medical instrument to at least one gas reactive to the residue,
    wherein, during at least steps at (c) and/or (d), the residue is detected and/or quantified, by at least one sensor device, in at least a part of a gas flow evacuated from the deposition and/or analysis apparatus during steps (c) and (d) in an uninterrupted manner,
    wherein, in a condition that concentration of the residue detected and/or quantified at (c) and/or (d) exceeds a predetermined threshold, the medical instrument is reverted to a procedure of cleaning and/or sterilization by conventional methods, and
    wherein, in a condition that concentration of the residue detected and/or quantified at (d) pertains to a predetermined level, the medical instrument is subjected to disposal.

2. The method of claim 1, wherein the medical instrument thus obtained is pre-applied, at least partly, with a chemically deposited coating.

3. The method of claim 1, wherein a coating is pre-applied onto at least a part of said medical instrument by Atomic Layer Deposition (ALD).

4. The method of claim 1, wherein the medical instrument is exposed, at (c) to a pressure below 10 hPa.

5. The method of claim 1, wherein, at (d), said at least one gas contains a chemical substance reactive to the residue.

6. The method of claim 1, wherein the medical instrument is a multi-part medical instrument.

7. The method of claim 1, wherein, during at least steps at (c) and/or (d), the at least one sensor device is configured to detect and/or quantify an amount of at least one gaseous compound reactive to the residue and/or of the products of chemical reactions between the at least one gaseous compound and the residue, respectively.

8. The method of claim 1, wherein steps (c) and (d) are performed sequentially or simultaneously.

9. The method of claim 1, wherein the medical instrument is exposed, at (c) to a pressure below 1 hPa.

10. The method of claim 1, wherein the medical instrument is exposed, at (c) to a pressure below 0.1 hPa.

11. The method of claim 1, wherein the medical instrument is an endoscope device.

* * * * *